United States Patent [19]

Piccariello et al.

[11] Patent Number: 5,516,950
[45] Date of Patent: May 14, 1996

[54] METHOD FOR THE PRODUCTION OF D-CHIROINOSITOL

[75] Inventors: Thomas Piccariello; Gamini Samanaryke, both of Blacksburg, Va.

[73] Assignee: Insmed Pharmaceuticals, Inc.

[21] Appl. No.: 389,709

[22] Filed: Feb. 14, 1995

Related U.S. Application Data

[63] Continuation-in-part of Ser. No. 228,101, Apr. 15, 1994, Pat. No. 5,406,005.

[51] Int. Cl.$^6$ .................................................. C07C 35/18
[52] U.S. Cl. ........................ 568/833; 568/822; 568/832
[58] Field of Search .......................... 568/822, 832, 568/833

[56] References Cited

U.S. PATENT DOCUMENTS

| | | | |
|---|---|---|---|
| 2,615,053 | 10/1952 | Artz et al. | 568/833 |
| 3,270,064 | 8/1966 | Inaha et al. | 568/833 |
| 3,288,820 | 11/1966 | Argoundelis et al. | 568/833 |
| 5,091,596 | 2/1992 | Kannington et al. | 568/833 |
| 5,406,005 | 4/1995 | Piccariello | 568/833 |

Primary Examiner—Werren B. Lone

[57] ABSTRACT

The present invention relates to the synthesis of D-chiroinositol from a dialdose, comprising the steps of condensing the dialdose by an acyloin condensation reaction to form an inosose, protecting the carbon atoms at the 2, 3, 4 and 5 positions, reducing the ketone of the inosose and removing the protecting groups. In addition, a method of preparing mannodialdose from mannuronic acid is disclosed.

14 Claims, 4 Drawing Sheets

Bn=Benzyl

Bz=Benzoyl  camph=Camphoryl  Tf=Triflyl

Benzene: X=H
Chlorobenzene: X=Cl

METHOD FOR THE PRODUCTION OF D-CHIROINOSITOL

This application is a continuation-in-part of U.S. application Ser. No. 08/228,101, filed Apr. 15, 1994, now U.S. Pat. No. 5,406,005.

FIELD OF THE INVENTION

A lack of D-chiroinositol, DCI, one of nine stereoisomers of the inositol series, has been implicated in the etiology of insulin resistant diabetes or non-insulin dependant diabetes mellitus (NIDDM). When DCI has been administered to animal models of diabetes it has been shown to lower blood glucose and insulin levels. Use of DCI as a therapeutic agent in the treatment of NIDDM and the insulin resistant condition is expected to service a significant segment of the population. This invention relates to a de novo synthesis of DCI of a quantity and quality suitable for pharmaceutical use. There have been several syntheses reported for DCI. Unfortunately, the most efficient methodologies are not appropriate for this purpose.

In addition to DCI, the stereospecific synthesis of myoinositol and its phosphate(s), an important class of compounds involved in secondary cellular signalling, have proven to be laborious. This invention is also useful in the applied stereospecific syntheses of myoinositol derivatives and other inositol isomers. These inositol derivatives should be applicable to syntheses of higher order carbohydrates as well.

BACKGROUND OF THE INVENTION

DCI has shown promise as a therapeutic agent to treat insulin resistance and those conditions associated with the disease such as NIDDM. Although the dosage has not been accurately determined, previous studies on primate models indicate that 1 gram per day is a reasonable dose upon which to base initial forecasts. There are 14 million diagnosed NIDDM patients in the United States. It is estimated that 20% of the general population is genetically predisposed to insulin resistance and therefore it is expected that daily manufacturing capacities for DCI will need to approach megagram quantities.

DCI can be isolated in kilogram quantities from natural sources. One of these sources is the California sugar pine. It has been shown that a 15 weight percent of pinitol (the 3-O methyl ether of DCI) can be extracted from the sawdust of this tree's stump. Pinitol can easily be converted to DCI in quantitative yield. With a yield of 1 kg/stump, an estimated 35 million stumps per year will be needed to supply the United States market demand with DCI (this calculation does not incorporate the fact that the stump ideally should be aged 5 years or more). Therefore, it is unlikely that the projected demand of DCI will be satisfied through this source.

DCI is also 40% of the antibiotic kasugamycin and is easily cleaved and purified from the antibiotic. Sources for kasugamycin have yet to prove to be reliable or economical. Attempts to produce a viable strain of *S. kasugaensis* either by natural selection techniques or fermentation process modifications have yet to yield a desirable result.

There have been several reported syntheses of chiroinositol (or its easily converted methyl ether) and they either entail a series of exhaustive protection/deprotection steps or fail to give the pure D-chiro isomer in a reasonable fashion. Martin-Lomas, et. al., reported a synthesis of 1-0-methyl-D-chiroinositol from methyl glucopyranose (compound 1) utilizing the well-known Ferrier rearrangement (entry 1 of FIG. 1). This approach required that the glucose molecule be subjected to a 4-step protection sequence leading to compound 2 which when rearranged yielded the key intermediate compound 3. Converting compound 3 to 1-0-methyl-D-chiroinositol involved four synthetic steps. Demethylation, as described above, would require an additional step for a total synthesis of DCI in 10 steps.

Ozaki and coworkers devised an approach to DCI starting from glucuronolactone (a.k.a. glucurone, compound 4). This synthesis involves a total of 17 steps, involving seemingly unnecessary manipulations and utilizes exotic reagents such as titanium tetrachloride which is the key reagent in the sequence shown in entry 2 of FIG. 1. In 1990, Shen and coworkers synthesized DCI from myoinositol by selectively epimerizing the 3-L position of myoinositol as shown in entry 3 of FIG. 1. This was done in 5 steps, however, one of the steps yielded a relatively small amount of product and another step involved a labor intensive separation of diastereomers.

The last two syntheses of DCI (entry 4 of FIG. 1) reported are similar in that the key step is a *Pseudomonas putida* oxidation of benzene (which generates a meso compound) or chlorobenzene (which generates an optically active compound) to the cyclohexadienediol derivatives 10 and 11. A novel approach to convert 11 to DCI was used. The final product, however, was contaminated with alloinositol, another of the nine isomers of inositol.

SUMMARY OF THE INVENTION

Figure 1A:
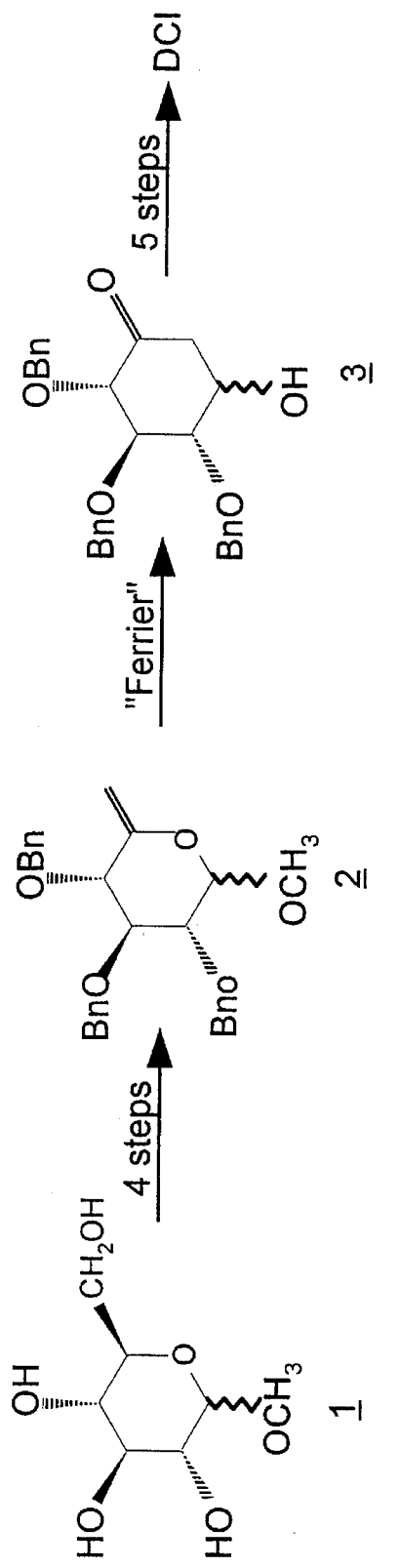
FIG. 1 shows prior art methods for the synthesis of chiroinositol.
Figure 1B:
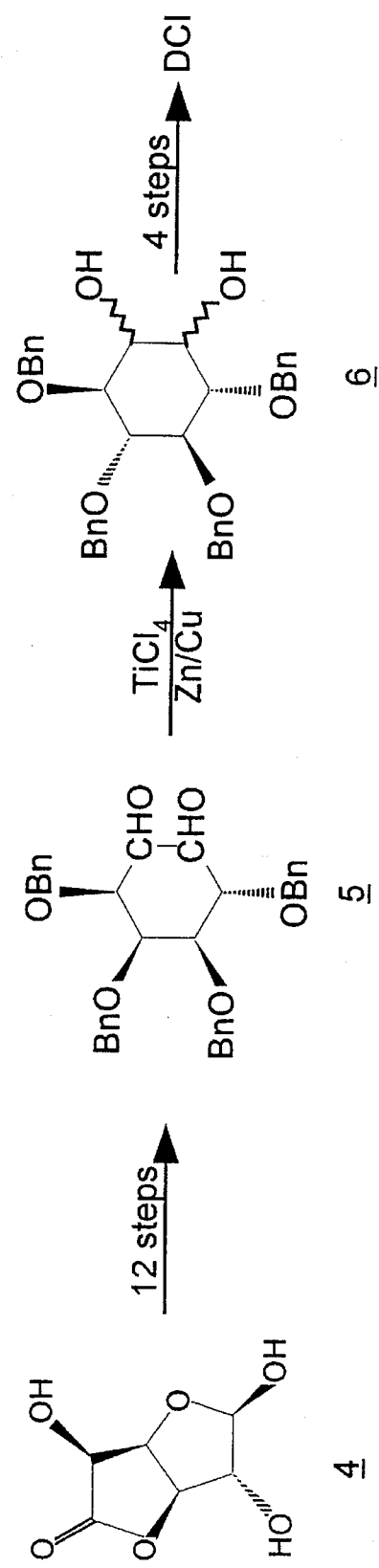
Figure 1C:
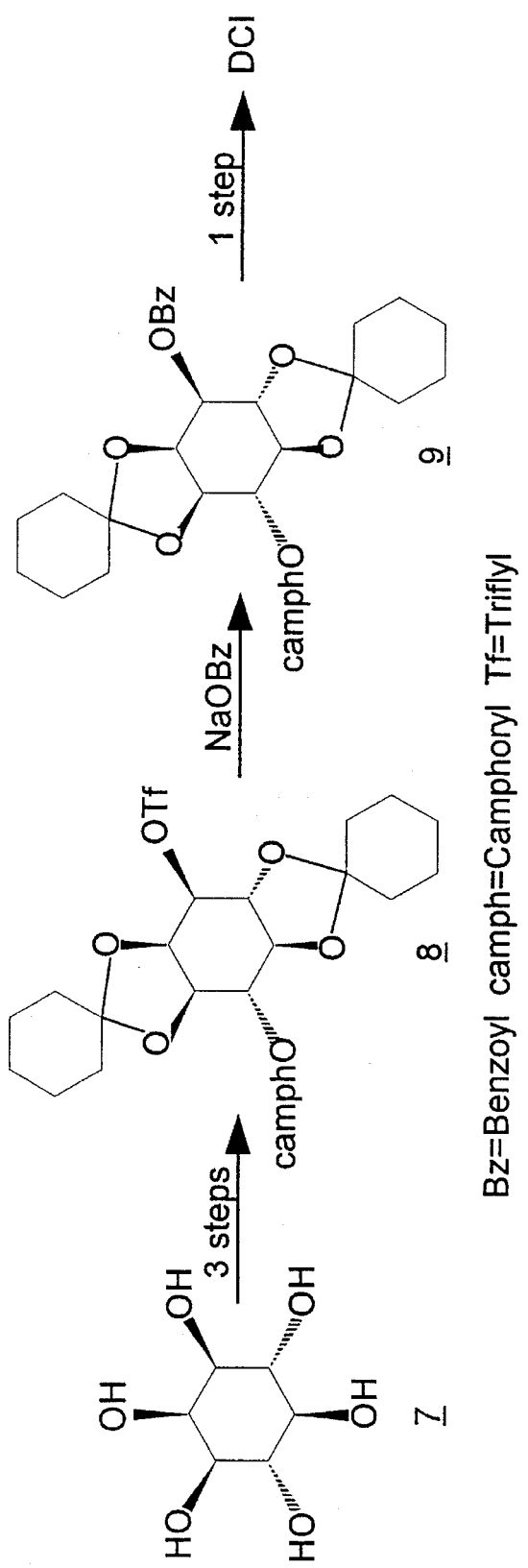
Figure 1D:
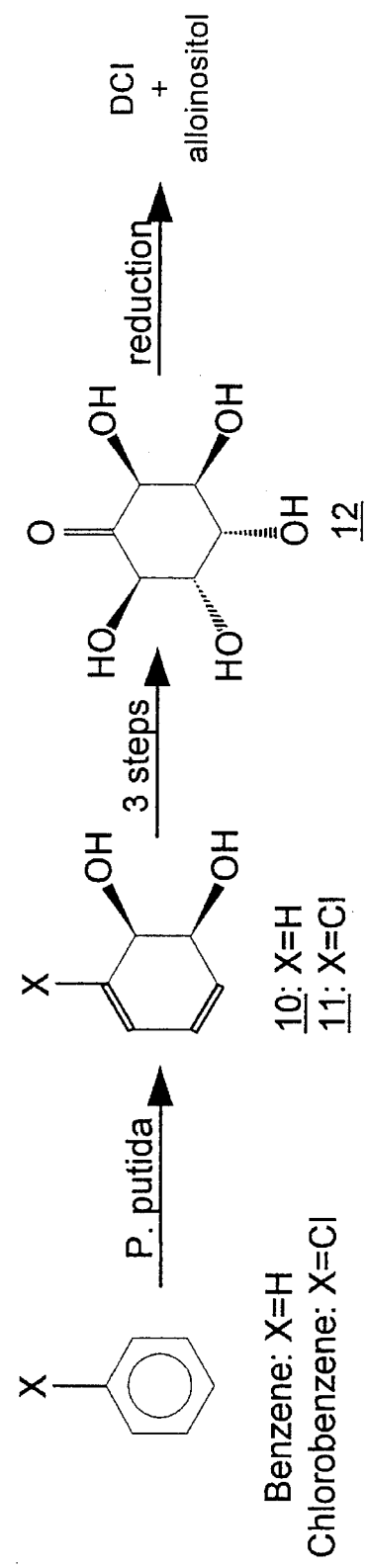

A novel methodology to synthesize inososes has been developed wherein a previously unknown intramolecular thiazolium acyloin condensation is utilized. The advantage of the present invention is that the use of the thiazolium salt allows the acyloin condensation to occur without the need for anhydrous conditions or the use of hazardous and expensive reagents such as sodium metal. A thiazolium salt catalyzed intramolecular acyloin condensation (analogous intermolecular reactions have been reported), and a new method for preparing inososes are disclosed. Additionally, a novel preparation of mannodialdose is disclosed.

DETAILED DESCRIPTION OF THE INVENTION

The three dialdoses that have been reported, glucodialdose, galactodialdose and mannodialdose (13) are obtainable by a variety of methods. Mannodialdose can be prepared by galactose oxidase catalyzed oxidation of mannose to mannodialdose or by reduction of mannuronic acid which is commercially available, albeit at a prohibitive cost. Reduced costs may be realized through improved extraction of mannuronic acid from alginic acid, but regioselective oxidation of mannose has proven to be a superior method. Galactodialdose preparation is well documented and utilizes the previously mentioned galactose oxidase. Glucodialdose has been prepared from glucose using photochemical methods and this method may be applicable to mannose as well, but it should be noted that scale-up of photochemical methods is, at best, plausible and that an even better preparation of glucodialdose and mannodialdose is from glucuronic acid (glucurone) and mannuronic acid, respectively.

Conversion of glucorone into glucodialdose in quantitative yield is known. Reducing mannuronic acid (or its lactone, 15), to mannodialdose incorporates a modification of this methodology, wherein mannuronic acid is reacted with either a trialkyl- or triarylboroxin, preferably trimethyl- or triethylboroxin, to form a boronate ester analogous to the boronate ester of glucorone. The boronate ester thus formed is then reduced with dialkylboron to form mannodialdose which can be used as a synthon for other stereoselective syntheses or as a chiral auxiliary.

Application of the thiazolium catalyzed acyloin condensation to mannodialdose will generate inososes 12 and 16. Formation of analogous inososes will come from glucodialdose and galactodialdose. When inososes 12 and 16 are protected as the diacetonide the major products are 17 and 18, respectively.

Refluxing an aqueous mixture of myoinositol and Raney nickel yields a mixture of myoinositol, chiroinositol and scylloinositol (plus the other 5 inositols in very low combined yield). The stereoselectivities observed in these reactions are presumably due to the fact that the isomers have adopted the preferred cis-trans configurations about the ring under thermodynamic conditions—a phenomenon most easily understood by recognizing that scylloinositol is the only isomer of the inositol series which is all-trans. In Raney nickel catalysis, a ketone reduction—alcohol oxidation equilibration sequence occurs. Imparting equilibrium conditions to 12 should result in a mixture of myoinositol, D-chiroinositol and scylloinositol with little or no alloinositol present.

Refluxing 17 and 18 with Raney nickel transforms the molecules such that the major product is 14 because positions 2, 3, 4 and 5 are protected and are therefore unaffected under these conditions. (The numbering system for inososes is as follows: the carbon with the highest oxidation state has the top priority and the next carbon in the hierarchy is the one which, when moving in a clockwise or counterclockwise fashion, is cis to the third carbon in line. The other three carbons are prioritized by the clockwise (or counterclockwise) direction dictated by the first three carbons.) Hydrolyzing 14 to remove the protecting groups will generate DCI.

Figure 3:
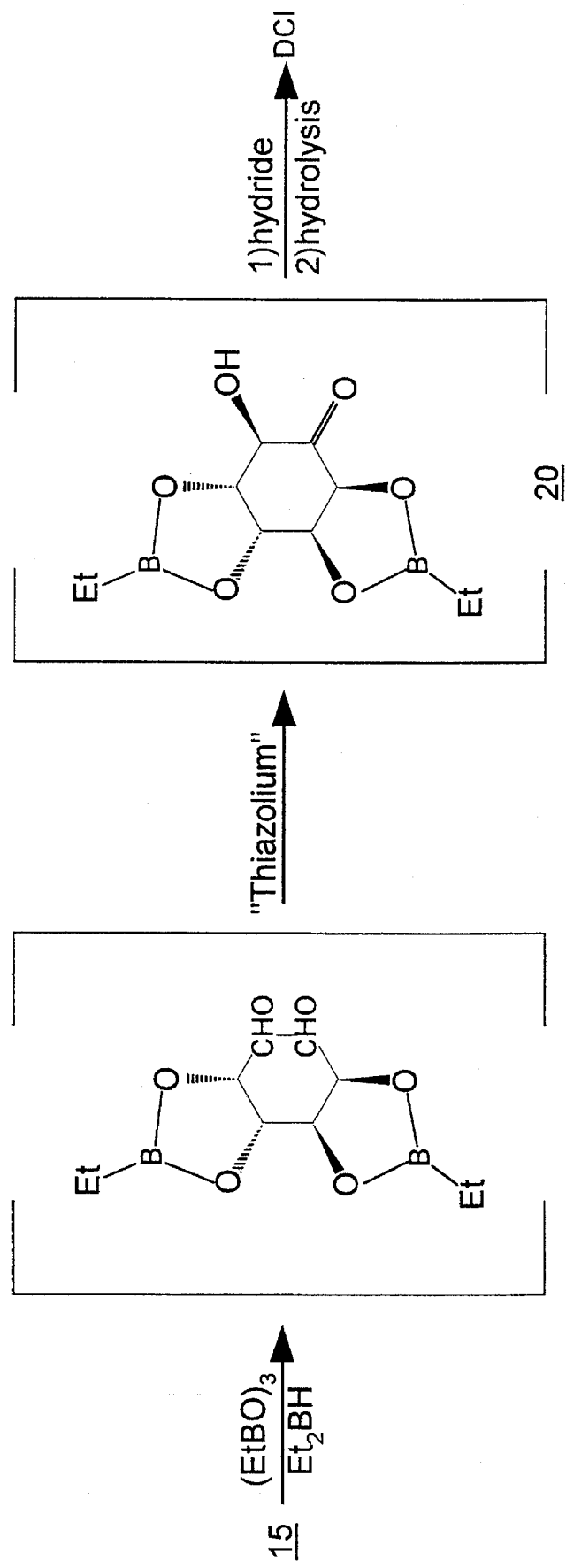
FIG. 3 shows the total synthesis of D-chiroinositol by a second embodiment of the present invention.

Alternatively, the inososes 12 and 16 can be protected as the boron ketal (for example: 12 becomes 20) where stereoselective reduction with a hydride transfer reagent such as sodium borohydride can occur (FIG. 3). By taking advantage of the valence unsaturation of the boron atom on the ketal, the hydride can be directed to the most sterically hindered face which, when deprotected, produces DCI. This is contrary to what is observed with hydride reduction of 12 where hydride attack occurs from the least hindered face and thus generates the undesired alloinositol product.

Figure 2:
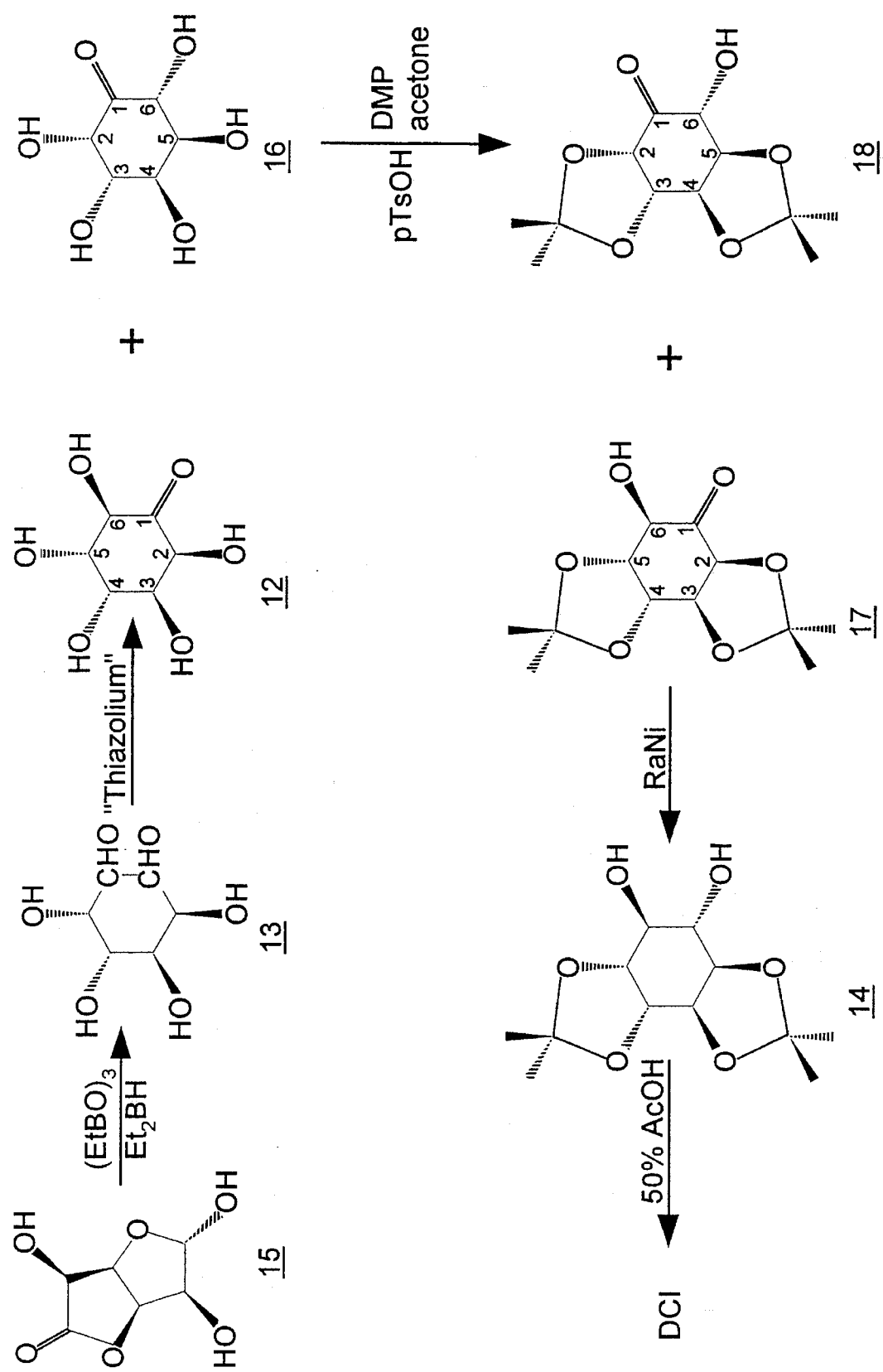
FIG. 2 shows the total synthesis of D-chiroinositol from mannodialdose by a first embodiment of the present invention.

The total synthesis of DCI from mannodialdose is shown in FIG. 2 and is done in 5 steps. It may be reduced to a one pot synthesis if one uses the boron protecting groups in step 1 to carry into the subsequent steps as shown in FIG. 3.

We claim:

1. A method for the synthesis of mannodialdose from mannuronic acid comprising the steps of:
   a. reacting mannuronic acid with a trisubstituted-boroxin to form a boronate ester; and
   b. reducing the boronate ester with dialkylboron to form mannodialdose.

2. The method of claim 1 wherein the substituent on the boroxin is selected from the group consisting of alkyl and aryl groups.

3. The method of claim 1 wherein the substituent on the boroxin is selected from the group consisting of ethyl and methyl.

4. A method for the synthesis of an inosose from a dialdose, comprising condensing the dialdose by an acyloin condensation reaction catalyzed by a thiazolium salt.

5. The method of claim 4 wherein the thiazolium salt is substituted at the 3-position with an alkyl or aryl group.

6. The method of claim 5 wherein the thiazolium salt is substituted at the 3-position with a benzyl group.

7. The method of claim 4 wherein the thiazolium salt is substituted at the 5-position with an alkyl, aryl or halo group.

8. The method of claim 7 wherein the thiazolium salt is substituted at the 5-position with a hydroxyethyl group.

9. The method of claim 4 wherein the dialdose is mannodialdose and the inosose is D-chiroinosose.

10. A method for the synthesis of an inositol from an inosose, comprising the steps of:
    a. protecting the carbon atoms at the 2, 3, 4 and 5 positions of the inosose by forming a first five-membered ring which incorporates carbons 2 and 3, and a second five-membered ring which incorporates carbons 4 and 5;
    b. reducing the ketone of the inosose to form a diol; and
    c. removing the protecting groups by subjecting the diol to acid catalyzed hydrolysis.

11. The method of claim 10 wherein the ketone of the inosose is reduced under equilibrating conditions by refluxing the inosose in the presence of Raney nickel.

12. The method of claim 10 wherein the first and second five-membered rings comprise a carbon ketal and the ketone of the inosose is reduced under kinetic conditions by subjecting it to a hydride transfer reagent.

13. The method of claim 10 wherein the first and second five-membered rings comprise a boron ketal and the ketone of the inosose is reduced under kinetic conditions by subjecting it to a hydride transfer reagent.

14. The method of claim 10 wherein the inosose is D-chiroinosose and the inositol is D-chiroinositol.

* * * * *